(12) United States Patent
Smith

(10) Patent No.: US 7,998,089 B2
(45) Date of Patent: Aug. 16, 2011

(54) METHOD OF MAKING A GUIDE WIRE BASED ASSEMBLY AND REUSING AN ENERGY SOURCE

(75) Inventor: Leif Smith, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 11/937,123

(22) Filed: Nov. 8, 2007

(65) Prior Publication Data

US 2009/0124880 A1 May 14, 2009

(51) Int. Cl.
*A61B 5/00* (2006.01)
*A61B 5/02* (2006.01)
*A61M 25/00* (2006.01)

(52) U.S. Cl. ........ 600/585; 600/300; 600/486; 600/488; 600/561

(58) Field of Classification Search .................. 600/587, 600/300, 486, 488, 561
See application file for complete search history.

(56) References Cited

U.S. PATENT DOCUMENTS

| | | | | |
|---|---|---|---|---|
| 4,967,753 A * | 11/1990 | Haase et al. | ................... | 600/468 |
| 5,213,619 A * | 5/1993 | Jackson et al. | ..................... | 134/1 |
| 5,318,533 A | 6/1994 | Adams et al. | | |
| 5,686,808 A * | 11/1997 | Lutz | ............................... | 320/110 |
| 5,687,717 A * | 11/1997 | Halpern et al. | ............... | 600/300 |
| 5,897,834 A * | 4/1999 | Lawrence et al. | .............. | 422/424 |
| 5,938,623 A * | 8/1999 | Quiachon et al. | ............ | 600/585 |
| 6,125,290 A * | 9/2000 | Miesel | ............................ | 600/325 |
| 6,167,763 B1 | 1/2001 | Tenerz et al. | | |
| 6,221,012 B1 * | 4/2001 | Maschke et al. | ............... | 600/301 |
| 6,336,906 B1 * | 1/2002 | Hammarstrom et al. | ...... | 600/585 |
| 6,387,043 B1 * | 5/2002 | Yoon | ............................... | 600/109 |
| 6,615,067 B2 * | 9/2003 | Hoek et al. | ..................... | 600/381 |
| 6,623,418 B2 * | 9/2003 | Smith | ................................. | 600/3 |
| 6,667,725 B1 * | 12/2003 | Simons et al. | ................. | 343/895 |
| 6,689,056 B1 * | 2/2004 | Kilcoyne et al. | .............. | 600/300 |
| 6,767,327 B1 * | 7/2004 | Corl et al. | ...................... | 600/486 |
| 6,926,674 B2 * | 8/2005 | Tenerz et al. | ................... | 600/486 |
| 6,939,313 B2 * | 9/2005 | Saadat et al. | .................. | 600/587 |
| 6,960,968 B2 * | 11/2005 | Odendaal et al. | ............. | 333/219 |
| 6,970,742 B2 * | 11/2005 | Mann et al. | ...................... | 607/23 |
| 6,993,974 B2 * | 2/2006 | Tenerz et al. | ................... | 73/727 |
| 7,274,956 B2 * | 9/2007 | Mott et al. | ...................... | 600/372 |
| 7,724,148 B2 * | 5/2010 | Samuelsson et al. | ....... | 340/573.1 |
| 2002/0077550 A1* | 6/2002 | Rabiner et al. | ................ | 600/439 |
| 2004/0034344 A1* | 2/2004 | Ryba | ............................... | 606/21 |
| 2004/0133089 A1* | 7/2004 | Kilcoyne et al. | .............. | 600/350 |

(Continued)

FOREIGN PATENT DOCUMENTS

DE    10 2005 003 171 A1    8/2006

(Continued)

*Primary Examiner* — Max Hindenburg
*Assistant Examiner* — Sean P Dougherty
(74) *Attorney, Agent, or Firm* — Foley & Lardner LLP

(57) ABSTRACT

A transmitter unit with a detachable energy source is provided for a sensor guidewire. The transmitter unit is adapted to be connected to a proximal end of a sensor guidewire provided, at its distal end, with a sensor to measure a physiological parameter inside a patient. In some embodiments, the transmitter unit is adapted to wirelessly communicate by a communication signal with a communication unit, arranged in connection with an external device, in order to transfer measured physiological data to the external device. The detachable energy source can be a battery pack provided with connecting electrical connecting surfaces. Preferably, the connection is protected from penetrating fluids by a protective seal.

7 Claims, 3 Drawing Sheets

U.S. PATENT DOCUMENTS

| | | |
|---|---|---|
| 2005/0197585 A1* | 9/2005 | Brockway et al. ............ 600/486 |
| 2005/0272974 A1* | 12/2005 | Iddan ............................ 600/106 |
| 2006/0009817 A1* | 1/2006 | Tulkki ............................. 607/60 |
| 2006/0030771 A1* | 2/2006 | Levine et al. ................. 600/424 |
| 2006/0068360 A1 | 3/2006 | Boulais |
| 2006/0079740 A1* | 4/2006 | Silver et al. .................. 600/309 |
| 2006/0079880 A1 | 4/2006 | Sage et al. |
| 2006/0127561 A1* | 6/2006 | Griffin et al. .................. 427/2.1 |
| 2006/0206002 A1* | 9/2006 | Frassica et al. ............... 600/101 |
| 2008/0041394 A1* | 2/2008 | Swann et al. ................ 128/831 |
| 2008/0091089 A1 | 4/2008 | Guillory et al. |
| 2008/0119758 A1* | 5/2008 | Samuelsson et al. ......... 600/561 |
| 2008/0200770 A1* | 8/2008 | Hubinette ..................... 600/300 |
| 2009/0069671 A1* | 3/2009 | Anderson ..................... 600/424 |
| 2009/0082678 A1* | 3/2009 | Smith ........................... 600/486 |
| 2009/0088650 A1* | 4/2009 | Corl .............................. 600/486 |

FOREIGN PATENT DOCUMENTS

| | | |
|---|---|---|
| WO | WO 2004/004176 A1 | 1/2004 |
| WO | WO 2005/086753 A2 | 9/2005 |

* cited by examiner

METHOD OF MAKING A GUIDE WIRE BASED ASSEMBLY AND REUSING AN ENERGY SOURCE

FIELD OF THE INVENTION

The present invention relates generally to a removable energy source for sensor guidewires and in particular to a detachable battery pack located on or at the transceiver unit in such an assembly.

BACKGROUND OF THE INVENTION

In many medical procedures, various physiological data within the body of a patient need to be monitored and analyzed. Typically, these data are physical in nature—such as pressure, temperature, and flow rate—and need to be monitored in a safe, reliable and accurate way. In the prior art, it is known to mount a sensor on a guidewire or catheter and to position the sensor via the guidewire in a blood vessel in a living body to detect such a physical parameter. The sensor includes elements that are directly or indirectly sensitive to the parameter. Numerous patents describing different types of sensors for measuring physiological parameters are assigned to the assignee of the present patent specification. For example, temperature can be measured by observing the resistance of a conductor having temperature sensitive resistance as described in U.S. Pat. No. 6,615,067. Another exemplifying sensor may be found in U.S. Pat. No. 6,167,763, in which blood flow exerts pressure on the sensor which delivers a signal representative of the exerted pressure. The entire contents of these patents are incorporated herein by reference for the devices and methods disclosed therein.

The raw signal generated by the sensor located within the body is transmitted to an external device, in which the signal is re-translated into physiological data, which is processed and the results continuously displayed on e.g. a monitor and/or saved. In order to power the sensor and communicate signals representing the measured physiological variable to an external device, one or more cables or leads for transmitting the signals are connected to the sensor, and are routed along the guidewire to be passed out from the vessel to the external device, conventionally via physical cables. In addition, the guidewire is typically provided with a central metal wire (core wire) serving as a support for the sensor and (optionally) also as an electrical connection to the sensor, and a surrounding tubing. Hence, a sensor guidewire typically comprises a core wire, leads and protective tubing, as well as a distal coil or tube and a jacket housing encasing the sensor.

In order to eliminate the risks of having an electrically conductive device such as a pressure transducer connected both to a patient and to an electronic monitoring instrument, a wireless arrangement can be used, e.g. as described in US Patent Application Publication No. 2006/0009817, assigned to the present assignee. In the aforementioned patent application, the pressure sensor wire is adapted to be connected, at its proximal end, to a transceiver unit that is adapted to wirelessly communicate via a communication signal with a communication unit arranged in connection with an external device, in order to transfer measured pressure data to the external device. In addition to the advantage of electrical insulation, a wireless arrangement decreases the amount of cables and other electrical equipment present in the operating room, and also facilitates the use of a standardized communication unit capable of being connected to a wide range of external devices. This obviates the necessity to use a specific external device, possibly different from that which is already present in the operating room. However, in contrast to a conventional sensor guidewire assembly, the pressure sensor in a wireless arrangement is not in electrical connection with the external device. Therefore, an additional energy source is required, such as a battery or capacitor, to power the transceiver unit and the pressure sensor. Also in a wired sensor guidewire assembly, a battery can be used as an alternative or auxiliary power supply. The entire contents of this publication are incorporated herein by reference for the devices and methods disclosed therein.

SUMMARY OF THE INVENTION

Using a transceiver with an internal battery is not well-suited for use in a disposable single-use medical device intended for an extended procedure in a sterile environment, which is the normal situation for sensor guidewires. Therefore, an object of the present invention is to provide an energy source better adapted to the abovementioned conditions, for use with sensor guidewires and other medical devices wherein a sensor is inserted into a body cavity for measurement of a physiological parameter.

The present invention provides a detachable energy source for a sensor guidewire assembly. Furthermore, the energy source is adapted to a sterile manufacturing and handling process, and is easily disposable in an environmentally acceptable manner. In addition, the energy source can be adapted to be detached after completing a procedure, optionally recharged, re-sterilized and used in one or more subsequent sensor guidewire procedures. The energy source can be used in a wired or wireless setup in a sensor guidewire procedure.

In some embodiments the energy source comprises one or several batteries. The batteries can be enclosed in a sealed holder. The battery pack is connected to a transmitter or transceiver unit whereupon, in some embodiments, the unit is powered up, calibrated and can optionally indicate by a light or sound signal that the assembly is ready for use.

It is also an object of the present invention to provide a method of making a guide wire assembly. The guide wire assembly comprises a pressure sensor wire, a transmitter unit, and an energy source which is attachable to and detachable from the transmitter unit via a fastening mechanism. The method comprises the steps of sterilizing the pressure sensor wire and sterilizing the energy source separate from the sterilizing of the pressure sensor wire before the energy source is attached to the transmitter unit. If the energy source is detachable, it can be recharged and sterilized for reuse.

DETAILED DESCRIPTION OF PREFERRED EMBODIMENTS

For ease of understanding, embodiments of the present invention are described in conjunction with a sensor guide wire. However, it is also within the scope of the invention to use a detachable energy source according to the present invention to power a transmitter unit connected to a sensor mounted on a catheter. Moreover, the transmitter unit is in many cases also a receiver unit. In those cases, the unit is, in fact, a transceiver unit, wherein the communication with the external device is a two-way communication. Thus, in the description below, unless explicitly stated, a transceiver unit can be exchanged for a transmitter unit.

In manufacturing a pressure sensor guide wire assembly, the pressure sensor wire and the transceiver unit must be able to be sterilized prior to use, which in practice has produced problems in the cases where an internal battery is present. Conventionally, gas sterilization using ethylene oxide is used for sensor guidewires. Specific precautions for each type of battery need to be taken in order to eliminate the risks of placing a battery connected to an electrical circuit in ethylene oxide. The present invention provides an improved sensor guidewire assembly which can be sterilized safely and also has environmental advantages.

For ease of description, examples of the present invention are illustrated in conjunction to an internal pressure sensor mounted in a wireless sensor guidewire assembly. However, it should be noted that it is within the scope of the invention to use a sensor adapted to measure other physiological parameters within the body, such as flow or temperature. It is also within the scope of the present invention to use a wired sensor guidewire assembly. Even though conventional, i.e. non-wireless, sensor guidewire assemblies are powered by an external power source, the present invention can eliminate the dependency on an external power source, or serve as an auxiliary energy source.

Figure 1:
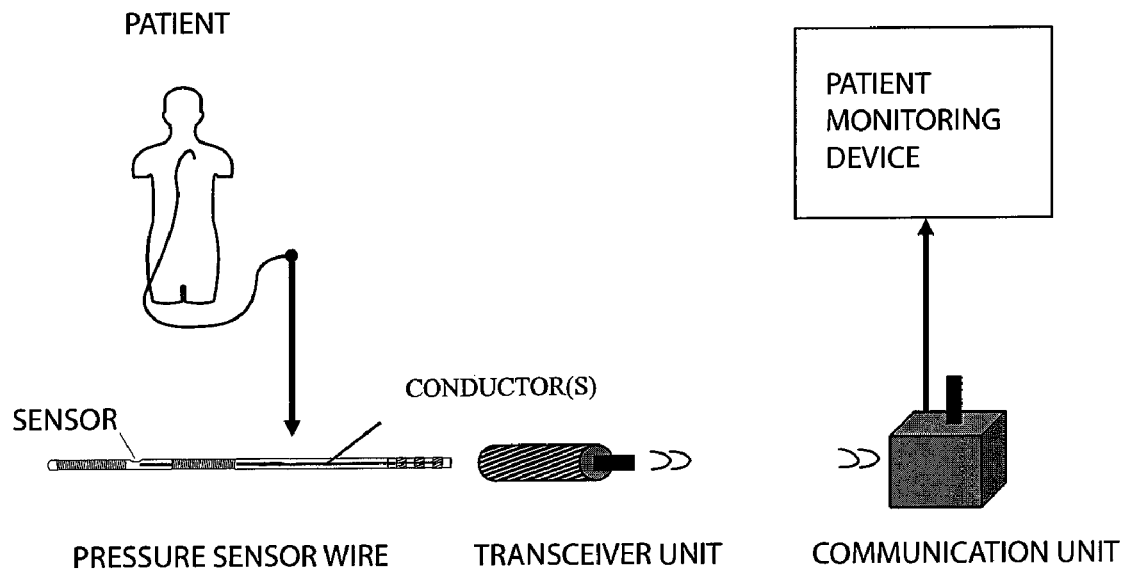
FIG. 1 illustrates one application of the present invention in a sensor guidewire assembly.

FIG. 1 is a schematic overview illustrating one application of the present invention. The pressure measurement system according to this embodiment of the present invention comprises a pressure sensor wire with a sensor adapted to measure pressure inside a patient, and to provide measured pressure data to an external device. The pressure sensor is located at a distal end portion of the pressure sensor wire and at least one conductor is configured to conduct an electrical sensor signal from the pressure sensor at the distal end portion of the pressure sensor wire to a proximal end portion of the pressure sensor wire. The pressure sensor wire is adapted to be connected, at its proximal end, to a transmitter or transceiver unit adapted to wirelessly communicate via a radio frequency signal with a communication unit arranged in connection with an external device, in order to transfer measured pressure data to the external device for analysis and display.

The external device may be a dedicated device or a patient monitoring device, preferably provided with a monitor, or a PC provided with relevant software and external connections to receive and to process the measured data from the pressure measurement system.

Figure 2:
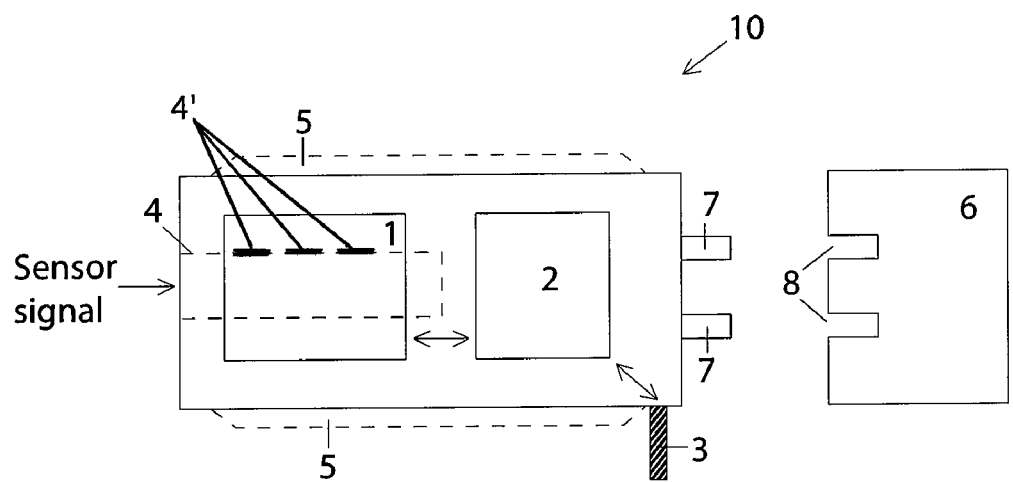
FIG. 2 shows a block diagram schematically illustrating a transmitter unit according to a preferred embodiment of the present invention.

FIG. 2 shows a block diagram schematically illustrating the transceiver unit 10 according to one embodiment of the present invention. As shown in FIG. 1, the transceiver unit is adapted to be connected to the proximal end of a pressure sensor wire provided, at its distal end, with a pressure sensor to measure pressure inside a patient. Preferably, the transceiver unit 10 comprises a sensor signal adapting circuitry 1, a communication module 2, connected to the adapting circuitry 1, that will handle the wireless communication with the communication unit via the antenna 3. The communication is preferably bi-directional, but can also be one-way.

The measured signal is communicated by the transceiver unit and transferred as a data stream to the communication unit at a prescribed frequency range (in the case where the communication signal is a radio frequency signal). The signal can also be an infrared signal, a light signal, an ultrasound signal or any wirelessly transmitted signal. In FIG. 2, the antenna 3 is illustrated as protruding outside the transceiver unit but may, as an alternative, be integrated into the housing of the transceiver unit. The pressure sensor wire is adapted to be inserted into an elongated aperture 4 of the transceiver unit 10. The aperture 4 is at its inner surface provided with a number of electrical connecting surfaces 4' to be connected to electrode surfaces at the proximal end of the pressure sensor wire when inserted into the aperture 4. The transceiver unit 10 can further be provided with a wire fastening means or mechanism (not shown) to firmly fixate the wire when correctly inserted into the aperture, if the transceiver unit is intended to be used as a torque device, as described below. As an alternative, the wire fastening means or mechanism can be constructed to hold the wire securely longitudinally, while allowing free rotation of the wire within the aperture 4.

When the pressure sensor wire is fixated to the transceiver unit, the unit may be used as a torque device when guiding the pressure sensor wire during insertion into a patient. Preferably the transceiver unit is provided with gripping means or structure 5, e.g. in the form of one or many elongated ribs on the outer surface of the transceiver unit, or by providing the transceiver unit with a roughened surface. In this context it should be mentioned that in the figures, the transceiver unit 10 and corresponding battery pack 6 (described below) are illustrated as having a generally round cross-sectional shape. However, it should be noted that it is within the scope of the invention to provide a transceiver unit and corresponding battery pack with any cross sectional shape. Using, for example, an octagonal cross-sectional shape, will provide for easier manipulation when using the transceiver unit as a torque device.

The transceiver unit is further provided with an attachable and detachable battery pack 6. Notably, the battery pack 6 is delivered separated from the transceiver unit and attached just prior to initiation of the surgical procedure. The battery pack is preferably encapsulated to ensure easy sterilization as well as easy transport, handling and connection. The battery pack 6 can be hermetically sealed if desired. The battery pack 6 is also provided with electrical connecting surfaces 8 constructed so as to fit the corresponding electrical contact members 7 on the transceiver unit 10. The battery pack 6 can be connected to the transceiver unit 10 by any type of electrical connectors to mate electrical connections, such as, but not limited to, those described below.

In FIG. 2, the connection is illustrated as having extending plugs 7 on the transceiver unit and receiving apertures 8 on the battery pack 6. However, it is within the scope of the present invention to provide the opposite arrangement, i.e. extended plugs on the battery pack and apertures on the transceiver unit. The extended plugs can moreover have any cross-sectional shape, as long as the receiving apertures are adapted to accept the extended plugs. Furthermore, the extended plugs and receiving apertures can be constructed such that the extended plugs snap into place when fully inserted, so as to firmly attach the battery pack 6 to the transceiver unit 10.

Figure 3A:
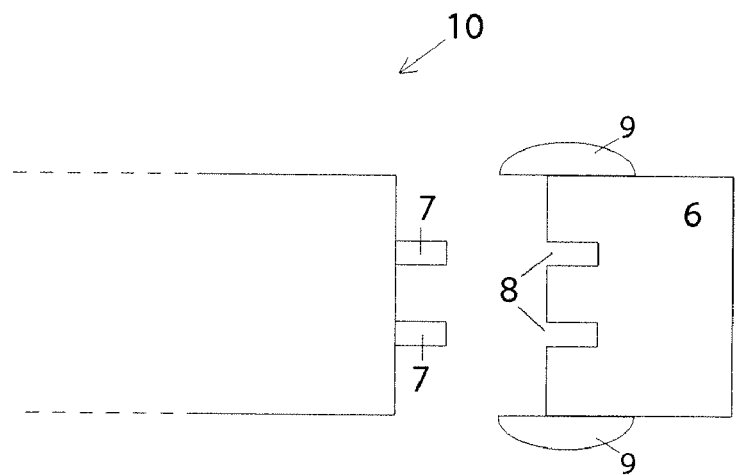
FIGS. 3a and 3b illustrate the present invention according to a further embodiment, in cross-sectional view and perspective view, respectively.
Figure 3B:
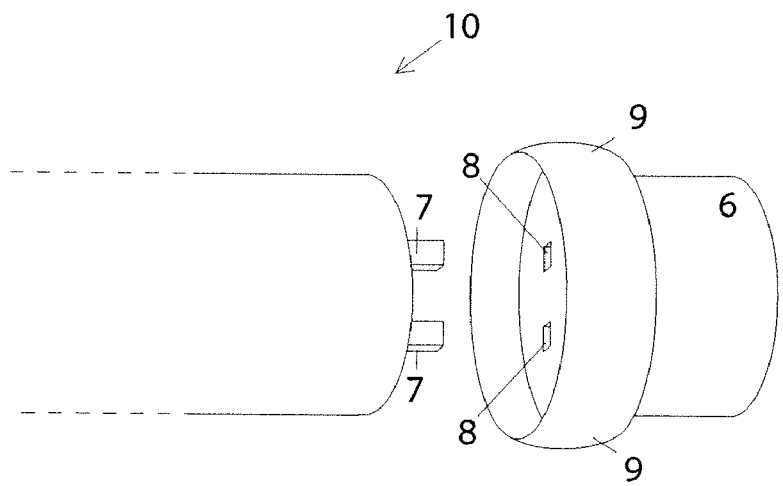

In a further embodiment, illustrated in cross-sectional view in FIG. 3a and in perspective view in FIG. 3b, the electrical connector is provided with a protective seal 9, preferably sealing the connection between the battery pack 6 and the transceiver unit 10 against fluids and other material when connected. The seal 9 is preferably elastic and can comprise rubber, silicone or any other material used to seal openings against penetrating fluids. Furthermore, the seal 9 is provided with an inner diameter slightly smaller than the outer diameter of the transceiver unit 10. The protective seal 9 can be any shape, as long as it seals the section containing electrical connecting surfaces effectively against penetrating material which could potentially short-circuit the connection. In the types of procedures described here, i.e. when using a sensor guidewire, there is normally blood and other fluids present and it is important in such an environment to avoid short-circuiting the system. The protective seal 9 can also be constructed so as to firmly hold the connector in place. Furthermore, the protective seal 9 can function as a shield against accidental contact by the user with the live electrical circuitry.

Figure 4:
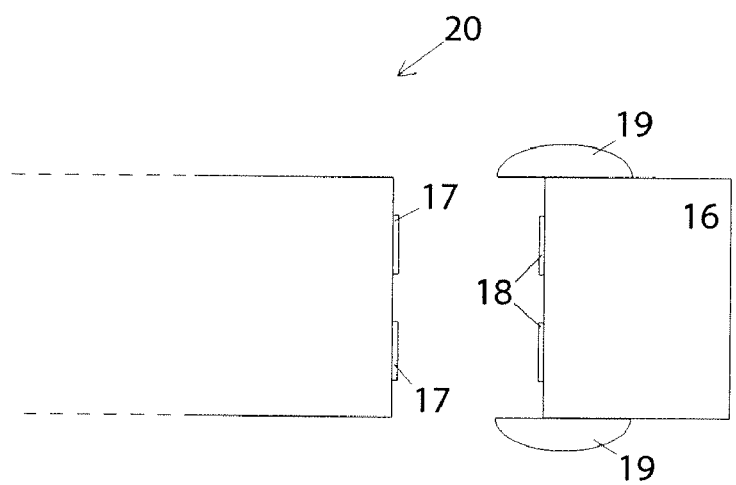
FIG. 4 illustrates the present invention according to another embodiment.

A further embodiment is illustrated in FIG. 4. As shown, the electrical connector can comprise electrical connecting surfaces or contact members 17, 18 placed flat against the transceiver unit 20 and the battery pack 16, respectively, which come in contact with each other when the battery pack is connected to the transceiver unit by any attachment means or mechanism (an example of which is described below). Using flat electrical contact members provides for easy cleaning of the connecting surfaces, which is an important characteristic when working with electrical equipment in a wet environment. Here, the connector is provided with a protective seal 19 which can also function to effectively hold the battery pack attached to the transceiver unit 20, and optionally also act as a shield against accidental contact by the user with the live electrical circuitry.

Figure 5:
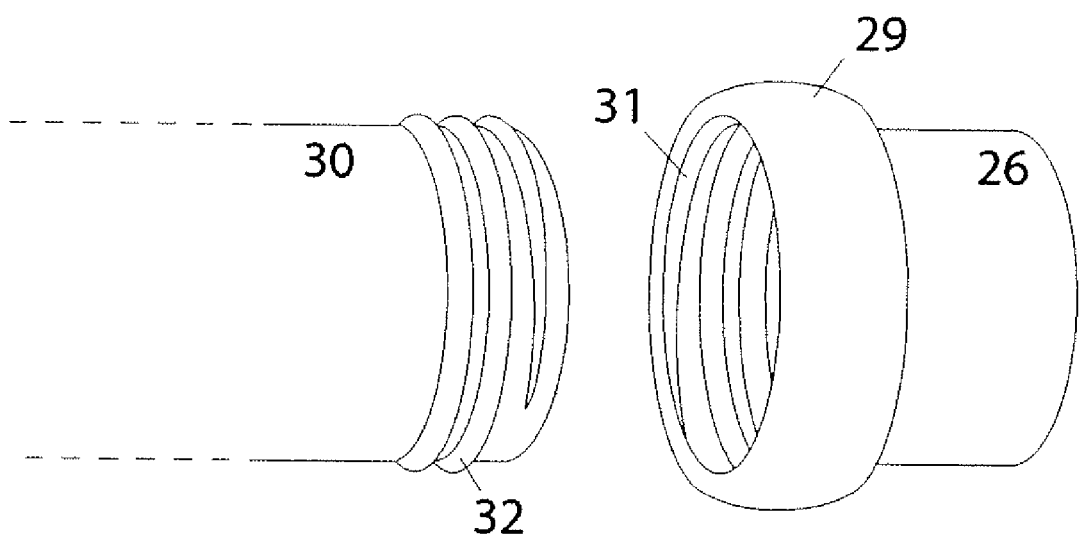
FIG. 5 illustrates the present invention according to yet another embodiment.

In addition to using the protective seal as an attachment mechanism using frictional forces, the battery pack can also be attached to the transceiver unit by any fastening mechanism, including the embodiment illustrated in FIG. 5. In this embodiment, the protective seal 29 again functions as a portion of an attachment means or mechanism. The inside of the protective seal 29 on the battery pack 26 is provided with internal threads 31 adapted to fit external threads 32 located on the transceiver unit 30. This embodiment provides very secure attachment, however the design of the electrical connecting surfaces (not shown in FIG. 5) has to be adapted to a rotating attachment procedure. For example, the flat contact members illustrated in FIG. 4 can be used in this embodiment. Other attachment means or structure besides threads include, but are not limited to, snaps, screws and barbs.

When the battery pack 6, 16, 26 has been attached to the transceiver unit, and the communication unit is connected to or integrated into the external device, the system is ready for use. According to one embodiment, the transceiver unit is activated and initiated when the battery pack is correctly attached to the unit. Upon correct attachment of the battery pack, the transceiver unit is powered up and preferably calibrated. In another embodiment, the transceiver unit will then try to establish a radio link connection with the communication unit. This is preferably performed by a conventional handshake procedure in order to identify the transceiver unit. In this embodiment, simply connecting the battery establishes that the connection is correctly made, that the battery is loaded and of the correct type and subsequently ensures that the system is initiated and ready for use, all in one step. In a further embodiment, the transceiver unit indicates activation, and optionally also successful calibration and/or connection with the communication unit, by e.g. a light or sound signal directly following attachment of the battery pack.

Battery packs 6, 16, 26 can comprise one or several batteries. The batteries can be of a non-rechargeable or a rechargeable type. The battery type can be any type in the art, including, but not limited to lithium primary battery, lithium ion (such as lithium iodine, lithium thionyl chloride, lithium carbon monofluoride or lithium silver vanadiumoxide) battery, alkaline manganese battery, other alkaline batteries, nickel cadmium battery, nickel metal hydride battery, mercury oxide battery, silver oxide battery, lead battery, zinc-air battery, carbon zinc battery, zinc manganese battery, manganese dioxide battery, and a capacitor cell.

Using a detachable battery pack, allows for an increased freedom in choice of sterilization methods during manufacture, as the energy source is disconnected from the electrical circuit, and the risks of processing live circuitry in the sterilization procedure are obviated. A battery pack according to the present invention, i.e. a battery pack which is not part of a live circuit (in other words, the battery pack is disconnected from any circuitry and therefore no current is flowing), can be sterilized using any sterilization method in the art, including but not limited to gas sterilization, autoclaving, radiation or alcohol treatment.

Using a detachable battery pack, in addition to making production and sterilization safer, is also positive from an environmental point of view. A battery pack can be transferred from one transceiver unit to another, enabling use of one battery pack for several interventional procedures. Preferably, the battery pack is re-sterilized and optionally recharged before subsequent use. Also, disposal of the battery is made easy when using a detachable battery pack.

Manufacture of a sensor guide wire entails calibration and testing of the final product before shipping to the user. When producing a sensor guide wire with a detachable battery pack, the manufacturer has the advantage of being able to use an energy source other than the energy source to be used during the surgical procedure for testing and calibrating the sensor during manufacture. Thus, the energy source needed for the surgical procedure is not depleted before initiation of the surgical procedure itself.

Although the present invention has been described with reference to specific embodiments it will be apparent for those skilled in the art that many variations and modifications can be performed within the scope of the invention as described in the specification and defined with reference to the claims below.

The invention claimed is:
1. A guide wire assembly, comprising:
    a pressure sensor guide wire having a pressure sensor located at a distal end portion of the pressure sensor guide wire and at least one conductor configured to conduct an electrical sensor signal from the pressure sensor at the distal end portion of the pressure sensor guide wire to a proximal end portion of the pressure sensor guide wire;
    a transmitter unit comprising a transmitter configured to generate a radio frequency signal containing pressure information from the pressure sensor; and
    an energy source which is attachable to the transmitter unit via a fastening mechanism,
    wherein the transmitter unit comprises a first housing and the energy source comprises a second housing and the first housing and the second housing are separate housings that are attachable to each other via the fastening mechanism,
    wherein the first housing and the second housing have respective ends which abut one another when the first housing is attached to the second housing via the fastening mechanism.
2. A guide wire assembly as set forth in claim 1, wherein the energy source is detachable from the transmitter unit via the fastening mechanism.

3. A guide wire assembly as set forth in claim 1, wherein the energy source is a rechargeable energy source.

4. A guide wire assembly as set forth in claim 1, wherein the transmitter unit further comprises a receiver module, to form a transceiver unit.

5. A guide wire assembly as set forth in claim 1, wherein the transmitter unit is adapted to communicate by the radio frequency signal with a communication unit, arranged in connection with an external device.

6. A guide wire assembly as set forth in claim 1, wherein the transmitter unit further comprises an aperture configured to receive the pressure sensor guide wire.

7. A guide wire assembly as set forth in claim 6, wherein the aperture comprises at its inner surface at least one electrical connecting surface configured to be connected to an electrode surface at the proximal end portion of the pressure sensor guide wire when inserted into the aperture.

\* \* \* \* \*